United States Patent [19]

Novak

[11] 4,442,420

[45] Apr. 10, 1984

[54] PARTIAL PRESSURE OF OXYGEN SENSOR-II

[75] Inventor: Robert F. Novak, Farmington Hills, Mich.

[73] Assignee: Ford Motor Company, Dearborn, Mich.

[21] Appl. No.: 429,413

[22] Filed: Sep. 30, 1982

[51] Int. Cl.³ .............................................. H01L 7/00
[52] U.S. Cl. ........................................ 338/34; 338/28
[58] Field of Search ............................ 338/34, 28, 13; 73/27 R; 422/98

[56] References Cited

U.S. PATENT DOCUMENTS

| | | | |
|---|---|---|---|
| 3,915,135 | 10/1975 | Kushida et al. | 338/34 X |
| 4,288,774 | 9/1981 | Takami et al. | 338/34 |
| 4,303,613 | 12/1981 | Yasuda et al. | 338/34 X |
| 4,308,518 | 12/1981 | Hattori et al. | 422/98 X |
| 4,338,281 | 7/1982 | Treitinger et al. | 422/98 |
| 4,343,768 | 8/1982 | Kimura | 422/98 X |

*Primary Examiner*—C. L. Albritton
*Attorney, Agent, or Firm*—William E. Johnson; Olin B. Johnson

[57] ABSTRACT

A partial pressure of oxygen sensor which finds utility when inserted into an exhaust system of a hydrocarbon fuel burning device. The oxygen sensor includes a mounting body both (a) threaded on one end for securement to the exhaust system, and (b) having a cylindrical configured bore extending along a central axis thereof. A heated sensing element is also provided which includes a ceramic support, a resistance heater element, and a titania dioxide sensor element in juxtaposition to the resistance heater element. An insulator body having a cylindrical configuration receives the heated sensing element therewithin. The insulator body is mounted in the cylindrical configured bore of the mounting body in a manner that the heated sensing element projects beyond a threaded end of the mounting body. A protection device is provided over the leading portion of the heated sensing element, this protection device also providing (a) an opening therein through which exhaust gases flow, and (b) a seat which accurately locates the heated sensing element therewithin. Electrical connections are made at the rear end of the mounting body to the resistance heater element and the titania dioxide sensor. Further structure is provided for supporting and sealing the electrical lead wires and providing electrical connections in a manner that the heating element is connected to a source of voltage and the sensing element to a sensing circuit.

5 Claims, 10 Drawing Figures

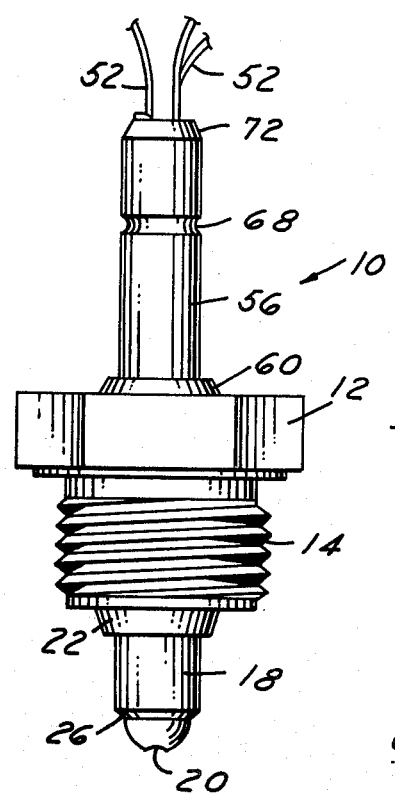
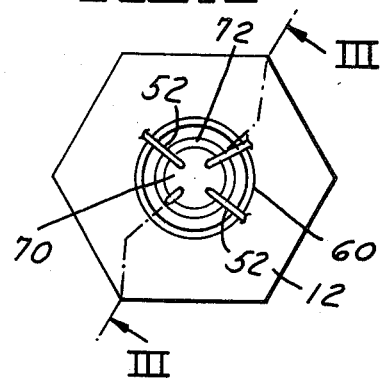
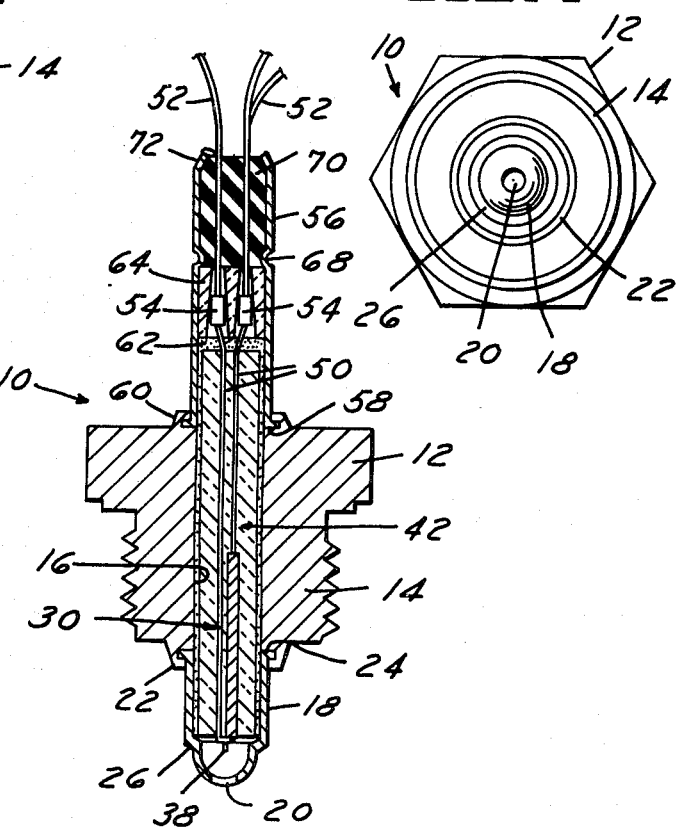

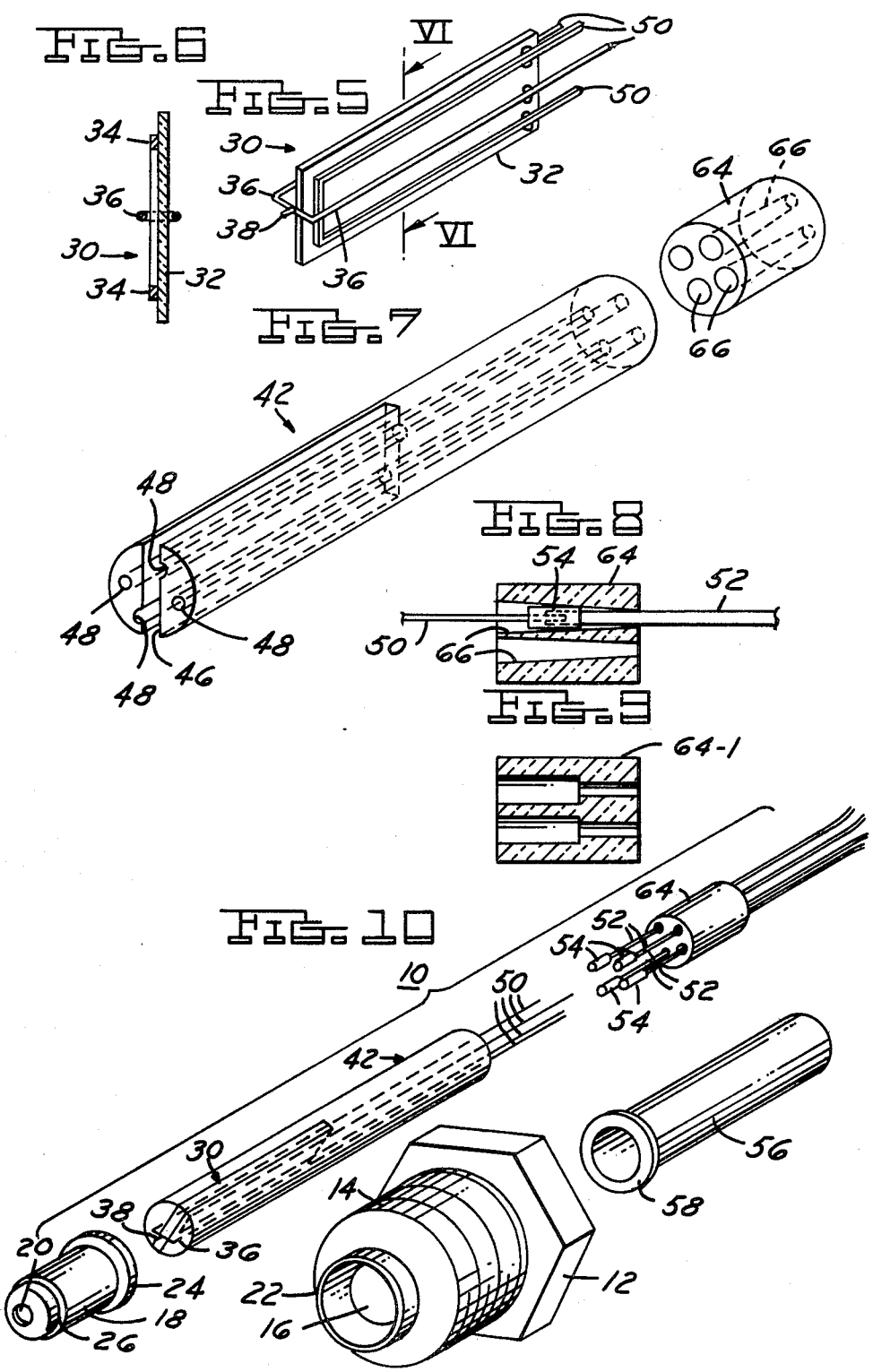

PARTIAL PRESSURE OF OXYGEN SENSOR-II

BACKGROUND ART AND PRIOR ART STATEMENT

The present invention is directed to the field of devices for controlling a hydrocarbon fuel burning device. In particular, the present invention is directed to a partial pressure of oxygen sensor which is inserted into an exhaust system which carries the exhaust gases from a hydrocarbon fuel burning device. The partial pressure of oxygen sensor is used with appropriate circuitry and mechanical devices associated therewith for controlling the amount of fuel which is introduced into the hydrocarbon fuel burning device. The amount of fuel being introduced into the device is a function of the amount of oxygen detected by the partial pressure of oxygen sensor in the exhaust gases flowing through the exhaust system.

Ceramic exhaust gas sensors of the electrically variable resistance type are known. For example, commonly assigned U.S. Pat. No. 3,893,230 by H.L. Stadler et al describes one such sensor fabricated from titania ceramic material. Also, commonly assigned U.S. Pat. No. 3,933,028 described such a sensor fabricated from cobalt monoxide ceramic material. Each of these sensor materials demonstrates an electrical resistance change as a function of the partial pressure of oxygen in the gaseous environment of the ceramic material when that material is located in the exhaust system of a hydrocarbon fuel burning device. The resistance changes may be measured by suitable electrodes. Each of the named sensing materials function best at an elevated temperature.

The present invention is directed to a particular structure for forming a partial pressure of oxygen sensor. The particular structure is one which provides a sensor of rugged construction, yet one which is efficient and effective in operation.

DISCLOSURE OF THE INVENTION

This invention is directed to a partial pressure of oxygen sensor and, more particularly, to a partial pressure of oxygen sensor for insertion into an exhaust system of a hydrocarbon fuel burning device.

In accordance with the teachings of this invention, the partial pressure of oxygen sensor comprises the following combination. A mounting body is formed of a metallic material. This mounting body is threaded on one end so that it may be secured to the exhaust system of the hydrocarbon fuel burning device. The mounting body has a cylindrical configured bore of a first diameter extending along a central axis thereof.

A first protection tube, having an opening therein, is secured to the threaded end of the mounting body. The protection tube has a stepped shoulder therein having an internal diameter smaller than the first diameter of the cylindrical bore of the mounting body.

The combination includes a heated sensing element of generally rectangular cross section which is constructed in the following manner. A ceramic support is provided and upon a leading portion thereof there is bonded a resistance heater element. A titania dioxide sensing element is also provided. This titania dioxide sensing element is supported on a sensing element supporting wire in a location in juxtaposition to the leading portion of the ceramic support. In this manner, the resistance heater element can heat the sensor element to a required temperature when a preselected voltage is applied across the resistance heater element.

The combination also includes an insulator body of ceramic material for supporting and protecting the heated sensing element. The insulator body has a shape of a right cylinder with a diameter of the cylinder being slightly less than the first diameter of the cylindrical configured bore of the mounting body. The insulator body has a slotted opening therein for receiving the heated sensing element therein, with the titania dioxide sensing element of the heated sensing element projecting beyond the leading portion of the insulator body. The insulator body receiving the heated sensing element therein is, in turn, received in the cylindrical configured bore of the mounting body in a manner such that the leading portion of the insulator body extends beyond the cylindrical bore to engage the stepped shoulder of the first protection tube. The first protection tube provided protection for the leading portion of the heated sensing element.

The combination includes a plurality of fine electrical lead lines. A pair of the fine lead lines is bonded to and extends from opposite ends of the resistance heater element. A pair of the fine lead lines is also bonded to and extends from opposite ends of the sensing element support wire. A plurality of electrical lead lines are also provided which are equal in number to the fine electrical lead lines. A plurality of crimped bands are also employed. Each of the crimped bands interconnects paired ones of the electrical lead lines and the fine electrical lead lines.

The combination also includes a second ceramic insulator body whigh has a plurality of passagways therein equal in number to the plurality of crimped bands. The passageways are so constructed and arranged that each of the passageways has an associated pair of the interconnected lead lines passing therethrough. Each of the crimped bands interconnecting the leads comes into locating engagement with the side walls defining the associated passageways in order to locate the interconnected leads positively within the passageway.

A second protection tube has one end thereof secured to an end of the mounting body not having the threads thereon. The second protection tube encloses and protects the second ceramic insulator body and the elements which are received within and pass therethrough.

A ceramic cement occupies a volume of the oxygen sensor between the second ceramic insulator body and a rear portion of the insulator body and heated sensing element received therein. A high temperature resistant sealant material occupies a volume between the second ceramic insulator body and a free end of the second protection tube. An electrical terminal is connected to the plurality of electrical lead lines for independently connecting the lead ines from the resistance heater element to a source of voltage and from the sensing element supporting wire to a sensing circuit.

BRIEF DESCRIPTION OF THE DRAWINGS

The novel features that are considered characteristic of the invention are set forth with particularity in the appended claims. The invention itself, however, both as to its organization and its method of operation, together with additional objects and advantages thereof, will best be understood from the following description of specific embodiments when read in conjunction with the accompanying drawings, wherein like reference characters indicate like parts throughout the several figures, and in which:

FIG. 1 is an elevational view of an assembled partial pressure of oxygen sensor in accordance with the teachings of this invention;

FIG. 2 is a plan view of the oxygen sensor of FIG. 1;

FIG. 3 is an elevational view taken along line III—III of FIG. 2 showing a cross section of the oxygen sensor of this invention;

FIG. 4 is a bottom view of the sensor of FIG. 1;

FIG. 5 is a perspective view of a heated sensing element;

FIG. 6 is a cross section view taken along line VI—VI of FIG. 5 showing additional details of the heated sensing element;

FIG. 7 is a perspective view of the insulator body and second insulator body used in the structure of this invention;

FIGS. 8-9 are different embodiments of the cross sectional construction of a second insulator body which may be used with the structure of this invention; and FIG. 10 is a schematic view of various elements making up the oxygen sensor of this invention prior to assembly of the structure.

BEST MODE AND INDUSTRIAL APPLICABILITY

The following description is what I consider to be a preferred embodiment of my partial pressure of oxygen sensor. The following description also sets forth what I now contemplate to be the best mode of building this oxygen sensor. This description is not intended to be a limitation upon the broader principles of this oxygen sensor and while preferred materials are used to illustrate the oxygen sensor in accordance with the requirements of the patents laws it does not mean that the oxygen sensor can be constructed only with the stated materials as others may be substituted therefor.

In accordance with the teachings of a preferred embodiment of this invention, a partial pressure of oxygen sensor, generally identified by the numeral 10, is shown in the drawings. The oxygen sensor is made up of a plurality of elements for forming the total combination. The plurality of elements will be described in greater detail hereinbelow. As is well known to those skilled in the art, the oxygen sensor is designed for insertion into an exhaust system of a hydrocarbon fuel burning device. The oxygen sensor serves as a device for sensing the amount of oxygen in the exhaust gases. The oxygen sensing device draws a variable amount of current in response to the amount of oxygen in the ambient surrounding the same, the current being drawn being an indication of the partial pressure of oxygen. The signal generated by the oxygen sensor is then fed to associated circuitry which uses the same to set an air/fuel metering device, such as a carburetor, to obtain a desired stoichiometric relationship between the air coming into the fuel burning device and the amount of fuel being burned. All of this type of operation is well known to a skilled artisan.

A first portion of the oxygen sensor 10 is a mounting body 12. The mounting body is formed of a metallic material and has a threaded portion 14 on one end thereof. The threaded portion is used for securing the oxygen sensor to the exhaust system of the hydrocarbon fuel burning device.

As is seen only in FIG. 3, the mounting body 12 has a cylindrical configured bore 16 extending along a central axis thereof. The cylindrical configured bore is for a purpose which will be described in greater detail hereinbelow.

A first protection tube 18 having an opening 20 therein is bonded to the lower end of the threaded portion 14 of the mounting body 12 as may best be seen in FIG. 3. A lip portion 22 of the mounting body 12 is folded over a lip portion 24 of the protection tube 18 in order to join the two elements together. The first protection tube also has a stepped shoulder 26 (best seen in FIG. 3) which has an internal diameter smaller than the diameter of the cylindrical configured bore 16 of the mounting body 12. The purpose of this stepped shoulder will be described in greater detail hereinbelow.

An elongated, heated sensing element, generally identified by the numeral 30 (best seen in FIG. 5), forms another element of the oxygen sensor 10. As is seen in FIG. 5, the heated sensing element 30 includes a ceramic support 32 of generally rectangular cross section preferably formed of alumina. A resistance heater element 34 is bonded to the ceramic support. This resistance heater element is formed from platinum or tungsten. The resistance heater element is so constructed and arranged that when a preselected voltage is applied thereto the heater will heat the sensing element 30 to a temperature range suitable for best operation of the device to detect oxygen. In the case of a titania sensor the temperature range is 600°-650° C. A sensing element supporting wire 36 (as best seen in FIG. 5) has a titania dioxide sensing element 38 bonded thereto. The details of construction of the heated sensing element 30 are set forth in a commonly assigned copending application entitled "Method of Making a Titania Dioxide Sensor Element-II", identified by the Ser. No. 429,411, filed on even date herewith.

The next element of the combination is an insulator body, generally identified by the numeral 42, formed of a ceramic material. This body is best seen in FIG. 7. The insulator body is formed to have a shape approximating a right cylinder with a diameter slightly less than the first diameter of the cylindrical configured bore 16 of the mounting body 12. The insulator body 42 has a slotted opening 46 in a leading end thereof for the purpose of receiving therewithin the ceramic support 32 of the heated sensing element 30. This construction is best seen in FIG. 10. The insulator body also has a plurality of openings 48—48 for a purpose which will be hereafter be described.

A plurality of fine electrical lead lines 50—50 are used to make electrical contact to the resistance heater element 34 and the titania dioxide sensing element 38. A pair of the fine electrical lead lines is bonded to and extends from opposite ends of the resistance heater element 34 on the ceramic support 32. In a similar manner a pair of fine electrical lead lines is bonded to and extends from opposite ends of the sensing element support wire 36 upon which the titania dioxide sensing element 38 is bonded. When the heated sensing element is received within the insulator body 42, the plurality of fine electrical lead lines 50—50 extend through the openings 48—48 in the insulator body.

As will be best understood by reference to FIGS. 3 and 10, a plurality of electrical lead lines 52—52 are also provided which are equal in number to the number of fine electrical lead lines 50—50. A plurality of crimped bands 54—54 are independently used for interconnecting paired ones of the fine electrical lead lines 50—50 and the electrical lead lines 52—52. Paired lead lines are inserted within the band and the band 54 is then crimped in order to secure the lead lines therewithin.

In the normal assembly operation the heated sensing element 30 contained within the insulator body 42 would be dropped into the cylindrical configured bore 16 of the mounting body 12 until a leading portion of the insulator body comes into contact with the stepped shoulder 26 of the first protection tube 18, as is best seen in FIG. 3. In this condition the titania dioxide sensing element 38 is located and protected within the first protection tube 18, but is exposed to exhaust gases by means of the opening 20 in the first protection tube.

A second protection tube 56 (best seen in FIGS. 3 and 10) has a lip portion 58 by which it is sealed by means of a lip portion 60 to an end of the mounting body 12 not having the threaded portion 14 thereon. The second protection tube 56 encloses and protects an upper portion of the insulator body 42 and wires passing therethrough as well as additional structure which will be described below.

A ceramic cement 62 is provided between the upper portion of the insulator body 42 protected by the second protection tube 56 and a second ceramic insulator body 64, as is best seen in FIG. 3. Seen in FIG. 8, the second ceramic insulator body has a plurality of tapered passageways 66—66 passing therethrough. These passageways are so constructed and arranged that each of the passageways will have an associated pair of interconnected leads passing therethrough with the crimped band 54 interconnecting the leads coming into locating engagement with the side walls defining the passageways. This helps to support any load which may be placed on the wires by applying pressure to the electrical lead lines 52—52.

As previously stated, the ceramic cement 62 is introduced into the second protection tube 56 at a position above the insulator body 42. While the cement is still wet the second ceramic insulator body 64 is threaded onto electrical lead lines 52—52 and thereafter introduced through the top of the second protection tube and forced against the ceramic cement. Thereafter, the second protection tube is crimped at crimp 68 to hold the second ceramic insulator body in place.

After the crimping operation and after the ceramic cement 62 has been allowed to cure, the remainder of the second protection tube 56 is filled with a high temperature resistant sealant material 70, seen only in FIG. 3. The high temperature sealant material occupies a volume between the second ceramic insulator body 64 and a free end of the second protection tube 56. A preferred high temperature resistant sealant material can be, for example, a silicone RTV material suitable for high temperature environments; that is, environments heated to a temperature up to 300° C. This sealant material will seal the top of the oxygen sensor 10 against moisture and salt spray. As is best seen in FIGS. 1 and 3, a free end 72 of the second protection tube 56 is crimped around the high temperature sealant material 70 to complete the sealing of the oxygen sensor.

The electrical lead lines 52—52 extending from the free end 72 of the second protection tube 56 may be secured to any suitable electrical connector (not shown) so that those leads may be properly connected to required circuitry. For example, the electrical leads 52—52 associated with the resistance heater element 34 on the ceramic support 32 of the heated sensing element 30 should be connected to a source of voltage so that the heating circuit can be actuated to heat the oxygen sensor 10. In a similar manner the electrical lead lines 52—52 associated with the sensing element support wire 36 supporting the titania dioxide sensing element 38 should be connected by means of the suitable connector to a sensing circuit. In this manner the output of the titania dioxide sensor element may be applied to suitable circuitry whereby other mechanical portions of the hydrocarbon fuel burning device may be controlled so that the proper amounts of oxygen and fuel are being used in the system.

While a preferred embodiment of the invention has been illustrated and described, it will be obvious to those skilled in the art that various changes and modifications may be made without departing from the invention, and it is intended to cover in the appended claims all such modifications and equivalents as fall within the true spirit and scope of this invention.

I claim:

1. A partial pressure of oxygen sensor for insertion into an exhaust system of a hydrocarbon fuel burning device, comprising in combination:

a mounting body formed of a metallic material threaded on one end for securement to the exhaust system and having a cylindrical configured bore of a first diameter extending along a central axis thereof;

a first protection tube having an opening therein secured to said threaded end of said mounting body, said first protection tube having a stepped shoulder therein having an internal diameter smaller than said first diameter of said cylindrical bore;

a heated sensing element including: a ceramic support of generally rectangular cross section, a resistance heater element bonded to a leading portion of said ceramic support, a titania dioxide sensing element, and a sensing element supporting wire upon which said titania dioxide sensing element is supported in a location in juxtaposition to said leading portion of said ceramic support so that said resistance heater heats said sensor element to a required temperature when a preselected voltage is applied across said resistance heater element;

an insulator body of ceramic material, said insulating body having a shape of a right cylinder with a diameter slightly less than said first diameter of said cylindrical configured bore, said insulator body having a slotted opening for receiving said heated sensing element therein with said titania dioxide sensing element of said heated sensing element projecting beyond a leading portion of said insulator body, said insulator body receiving said heated sensing element therein being received in said cylindrical configured bore of said mounting body in a manner such that, said leading portion of said insulator body extends beyond said cylindrical bore to engage said stepped shoulder of said first protection tube, said first protection tube protecting said leading portion of said heated sensing element, said opening of said first protection tube permitting exhaust gases to flow into contact with said heated sensing element;

a plurality of fine electrical lead lines, a pair of said fine lead lines being bonded to and extending from said resistance heater element and a pair of said fine lead lines also bonded to and extending from said sensing element supporting wire;

a plurality of electrical lead lines equal in number to said fine electrical lead lines;

a plurality of crimped bands, each of said crimped bands interconnecting paired ones of said electrical lead lines and said fine electrical lines;

a second ceramic insulator body having a plurality of passageways therein equal in number to said plurality of said crimped bands, said passageways being so constructed and arranged that each of said passageways has an associated pair of said interconnected leads passing therethrough with said crimped band interconnecting the same coming into locating engagement with the side walls defining said associated passageway;

a second protection tube means having one end secured to an end of said mounting body not having said threads thereon for enclosing and protecting said second ceramic insulator body and elements received therein and passing therethrough;

a ceramic cement occupying a volume between said second ceramic insulator body and a rear portion of said insulator body and heated sensing element received therein;

a high temperature resistant sealant material occupying a volume between said second ceramic insulator body and a free end of said second protection tube means; and electrical terminal means connected to said plurality of electrical lead lines for independently connecting said lead lines as required to a source of voltage and to a sensing circuit.

2. The partial pressure of oxygen sensor as defined in claim 1, wherein each of said passageways of said second ceramic insulator body is of a tapered design in which a front face of each passageway has a diameter greater than an associated one of said crimped bands received therein and a back face of each passageway has a diameter less than an associated one of said crimped bands but greater than an associated one of said electrical lead lines passing therethrough.

3. The partial pressure of oxygen sensor as defined in claim 1 or claim 2, wherein said first protection tube has a plurality of openings therein.

4. The partial pressure of oxygen sensor as defined in claim 1, wherein each of said passageways of said second ceramic insulator body is of a stepped design in which a first portion of each passageway has a diameter greater than an associated one of said crimped bands received therein and a second portion of each passageway has a diameter less than an associated one of said crimped bands but greater than an associated one of said electrical lead lines passing therethrough.

5. The partial pressure of oxygen sensor as defined in claim 1 or claim 4, wherein said first protection tube has a plurality of openings therein.

* * * * *